US00PP36394P2

(12) United States Plant Patent
Hansoti

(10) Patent No.: US PP36,394 P2
(45) Date of Patent: Jan. 14, 2025

(54) ***SANSEVIERIA* PLANT NAMED 'Hansoti44'**

(50) Latin Name: *Sansevieria trifasciata*
Varietal Denomination: Hansoti44

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 18/426,493

(22) Filed: Jan. 30, 2024

(51) Int. Cl.
*A01H 5/12* (2018.01)
*A01H 6/12* (2018.01)

(52) U.S. Cl.
USPC ..... Plt./382

(58) Field of Classification Search
USPC ..... Plt./373, 382
See application file for complete search history.

*Primary Examiner* — Karen M Redden

(57) ABSTRACT

A new and distinct cultivar of *Sansevieria* plant named 'HANSOTI44' is disclosed, characterized by unusual twisted, curled, compact foliage arranged in flattened, spiral rosettes. The new cultivar is a compact "Birds Next" type *Sansevieria* forming small plants, reaching only about 12 cm in height at maturity. Plants require little water, having a moderate tolerance for drought, and are also tolerant of very wet conditions. Foliage is bright yellowish-cream, with a dark olive-green border with streaks of greyish-green. The new variety is a *Sansevieria*, typically produced as an indoor ornamental plant.

6 Drawing Sheets

Latin name of the genus and species: *Sansevieria trifasciata.*

Variety denomination: 'HANSOTI44'.

BACKGROUND OF THE INVENTION

The present invention relates to a new and distinct cultivar of *Sansevieria* plant, botanically known as *Sansevieria trifasciata*, of the family Asparagaceae, hereinafter referred to by the cultivar name 'HANSOTI44'.

*Sansevieria* is a monocotyledonous plant with fleshy, succulent leaves which are available in a huge range of species, varieties and cultivars as an outdoor ornamental plant (under tropical conditions) or as indoor plants.

The new *Sansevieria* 'HANSOTI44' was discovered and selected by the inventor, Ashish Hansoti, as a single aberrant side shoot within a planting of *Sansevieria trifasciata* 'Hansoti41', filed concurrently and having application Ser. No. 17/426,474, a "Hahnii" or "Birds Nest" type of *Sansevieria* grown at a nursery in Village Vangani, District Thane, Maharashtra State in Western India. 'HANSOTI44' originated as a naturally-occurring mutation of the *Sansevieria trifasciata* variety 'Hansoti41' in August of 2020.

Asexual reproduction of the new *Sansevieria* cultivar by vegetative cuttings was first performed in March 2021 at a commercial nursery in Village Vangani, District Thane, Maharashtra State in Western India. This first and subsequent propagation have shown that the distinctive combination of characteristics of the new cultivar are reproduced true to type as long as the propagation was done through side shoots (basal suckers) originating from the base of the originally discovered plant. Thus, it can be said that the new cultivar reproduces true to type through side shoots (basal suckers).

BRIEF SUMMARY OF THE INVENTION

The following traits have been repeatedly observed and are determined to be unique characteristics of 'HANSOTI44', which in combination distinguish this *Sansevieria* as a new and distinct cultivar:

1. Twisted, curved leaves forming a flat, relatively open, somewhat eccentric (when seen from top) spiral-form rosette, that stays vertically compact and gives a flat appearance as opposed to most other *Sansevieria trifasciata* 'Hahnii' cultivars where the leaves are straighter and more vertically oriented. Total mature-plant width in a 12 cm pot is 17 to 20 cm or more while the height above the pot is only 10 to 12 cm.
2. Leaf coloration and variegation pattern is also quite unique and very different from its parent, *Sansevieria trifasciata* 'Hansoti41'. Overall colour impression is of a bright yellowish-cream *Sansevieria* with dark olive-green border and streaks of greyish-green.
3. 'HANSOTI44' has foliage variegation pattern and colour that is unlike its parent's but it does have its parent's very unusual vertically—flat spiral foliage arrangement, giving an overall extremely distinctive and unique appearance.
4. Typical transverse banding seen in most *Sansevieria trifasciata* cultivars is indistinct and tends to blends into the creamy background but is more obvious in the dark green border where this border is broad and prominent.

Leaf width is quite variable and the strongest, healthiest plants have the widest leaves—this is true across all *Sansevieria trifasciata* cultivars known to the inventor. This variation means leaf width can be anything from 3 cm to 6 cm wide depending on season, growing conditions and plant vigour and plant age. Typically, the leaves are 10 to 16 cm long, ensiform but not erect; rather, most unusually, they are held quite horizontally. Leaves have a firm, waxy texture. The blades are thick and fleshy.

The new variety 'HANSOTI44' is a variety of *Sansevieria* in the group denominated as "Birds Nest" or 'Hahnii' types based on its origin and overall plant form. The new variety presents an average of 13 leaves per plant when it reaches maturity (about 3 months from rooted liner) but over time it can grow and accumulate many more leaves and increase in overall height.

The new variety is moderately drought tolerant and adapts well to conditions of bright light or heavy shade (exterior and interior). The intensity of leaf colour varies with exposure to light and the contrast is most intense under high light conditions.

The leaves show a variegated colouration, with broad green borders having a central area of cream interspersed with grey-green streaks. There is a very light central band of soft green buried under the epidermis in the centre of the cream area.

Each leaf has a marginal deep green band close to RHS Green 136A and this border band varies in width from just 2 mm, going up to 20 mm. Within this dark olive-green border, the leaf has an overall creamy coloration close to Yellow 4B or, very occasionally, nearer Yellow-Green 154B overlaid to varying degrees with streaks of grey-green similar to the border (close to Green 136A).

The backside of the leaves is also distinctive—a relatively thin 1 mm to 7 mm wide border of dark olive green with a visually uniform creamy golden coloration between them. Very occasionally this creamy central area is invaded by dark green stripes from 2 to 5 mm wide.

The typical *Sansevieria trifasciata* cross hatching, running across the width of the leaf, though seen on the top surface, is much subdued and indistinct and tending to blend into the surrounding cream. On the broader marginal bands this cross hatching is seen as a lighter band close to RHS Yellow-Green 147B with darker areas of Green 136A as noted above.

The underside of the leaf also has the typical *Sansevieria trifasciata* transverse cross hatching but this banding is very light and subtle; from lighter stripes near RHS Yellow 4D to darker stripes of Yellow 1C—observable only on close inspection.

Attached colour pictures are a better guide to the complex leaf arrangement and the overall colouration and pattern rather than written descriptions and are the best reference to compare the new plant invention 'HANSOTI44' to older and newer *Sansevieria trifasciata* 'Hahnii' mutants. The primary distinctive characteristics of 'HANSOTI44' are the unique curved, twisted leaves forming a flat, vertically compact disc and the unique variegation colour and pattern of these twisted leaves.

PARENTAL COMPARISON

Plants of the new *Sansevieria* 'HANSOTI44' are similar to plants of the parental cultivar, however, 'HANSOTI44' differs in the characteristics described in Table 1.

TABLE 1

| | Characteristic | Parent Cultivar 'Hansoti41' (PPAF) | New cv 'Hansoti44' |
|---|---|---|---|
| 1. | Leaf | 12 to 16 cm long, twisted and curved and held horizontally to form a vertically flat, spiral rosette | 12 to 16 cm long, twisted and curved and held horizontally to form a vertically flat, spiral rosette |
| 2. | Number of leaves | 10 to 12 leaves (fewer leaves) | 12 to 15 leaves (more leaves) |
| 3. | Variegation Pattern | Dark, olive-green bands on both sides with cream centres liberally streaked with grey green bands and darker green stripes. Overall look is of an olive-green rosette with occasional cream streaks. | Dark, olive-green bands on both sides with broad, full cream centre occasionally streaked with grey green bands and darker green stripes. Overall look is of a cream-colored rosette with occasional green streaks and dark green borders. |
| 4. | Border variegation | 5 to 15 mm wide dark green band | 1 to 7 mm wide dark green band |
| 5. | Central Variegation | 2 to 3 cm wide band of creamy yellow almost entirely covered by streaks and bands of grey-green and stripes of dark green. *S. trifasciata* transverse banding seen. | Very wide band of creamy yellow, fully covering the leaf blade between the border of dark green. Occasional streak of dark olive green crossing this expanse of yellow-cream. *S. trifasciata* transverse banding extremely indistinct and almost totally blending into the creamy yellow background. |

COMMERCIAL COMPARATOR

Plants of the new *Sansevieria* 'HANSOTI44' are similar to the commercial variety *Sansevieria trifasciata* 'Hansoti21', U.S. Plant Pat. No. 33,168. Plants of the new *Sansevieria* 'HANSOTI44' differ from plants of the commercial cultivar in the characteristics described in Table 2.

TABLE 2

| | Characteristic | Similar Cultivar 'Hansoti21' (Tornado) U.S. Plant Pat. No. 33,168 | New cv 'Hansoti44' |
|---|---|---|---|
| 1. | Leaf | 8 to 13 cm long (shorter) and 4-6 cm wide (wider) | 12 to 16 cm long, twisted and curved and held horizontally to form a vertically flat, spiral rosette |
| 2. | Number of leaves | 11 to 13 leaves (fewer leaves) | 12 to 15 leaves (more leaves) |
| 3. | Variegation Pattern | Creamy border band with green centres prominently marked with typical *S. trifasciata* transvers banding. | Dark, olive-green bands on both sides with broad, full cream centre occasionally streaked with grey green bands and darker green stripes. |
| 4. | Border variegation | 3 to 12 mm creamy band | 1 to 7 mm wide dark green band |
| 5. | Central Variegation | Only the transverse light green banding typical of *S. trifasciata* seen | Very wide band of creamy yellow fully covering the leaf blade between the border of dark green. Occasional streak of dark olive green crossing this expanse of yellow-cream. *S. trifasciata* transverse banding extremely indistinct and almost totally blending into the creamy yellow background. |

BRIEF DESCRIPTION OF THE PHOTOGRAPHS

The accompanying photographs illustrate the overall appearance of the new *Sansevieria* cultivar 'HANSOTI44' showing the colors as true as is reasonably possible with colored reproductions of this type. Colors in the photographs may differ slightly from the color value cited in the detailed botanical description which accurately describe the color of 'HANSOTI44'.

These pictures illustrate the plant form which is the unique characteristic of 'HANSOTI44' and at the same time demonstrates that plant coloration and variegation pattern is similar to several other *Sansevieria trifasciata* cultivars. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

Figure 1:
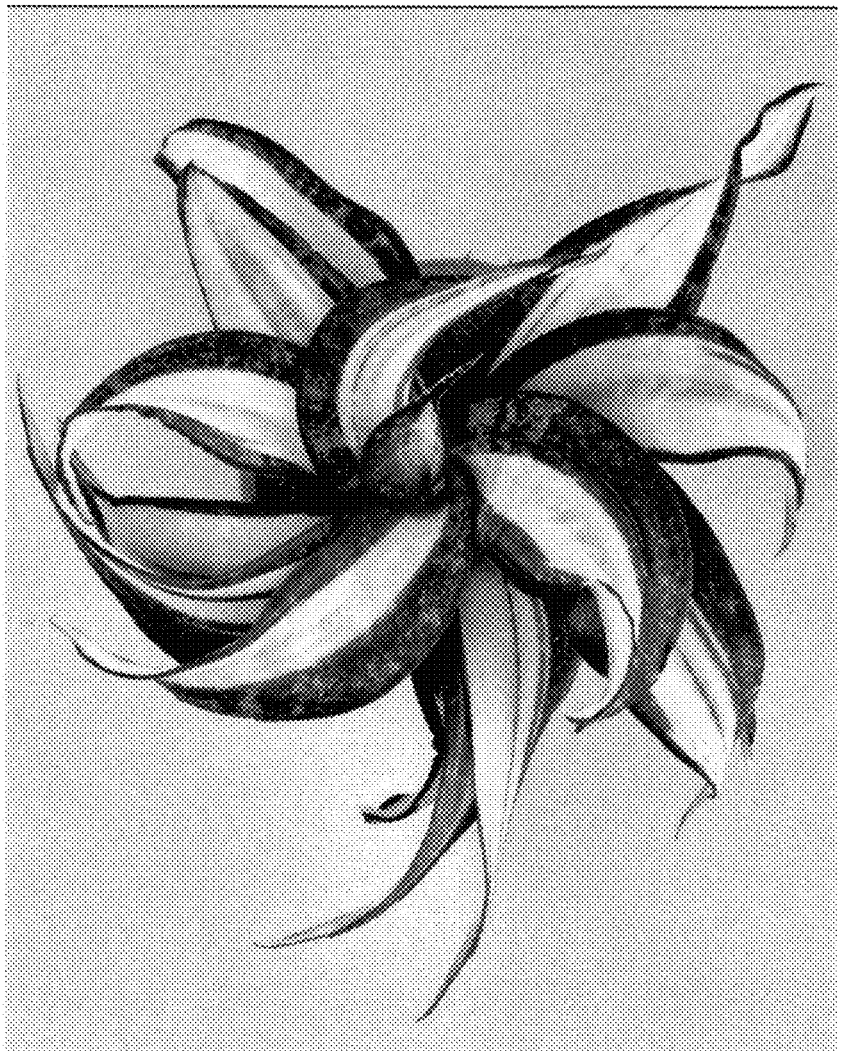
FIG. 1 shows a top view of a three-month-old (from rooted liner) plant of *Sansevieria* 'HANSOTI44' in a 12 cm diameter pot. The spiral rosette and variegation pattern and colour are distinctly seen.
Figure 2:
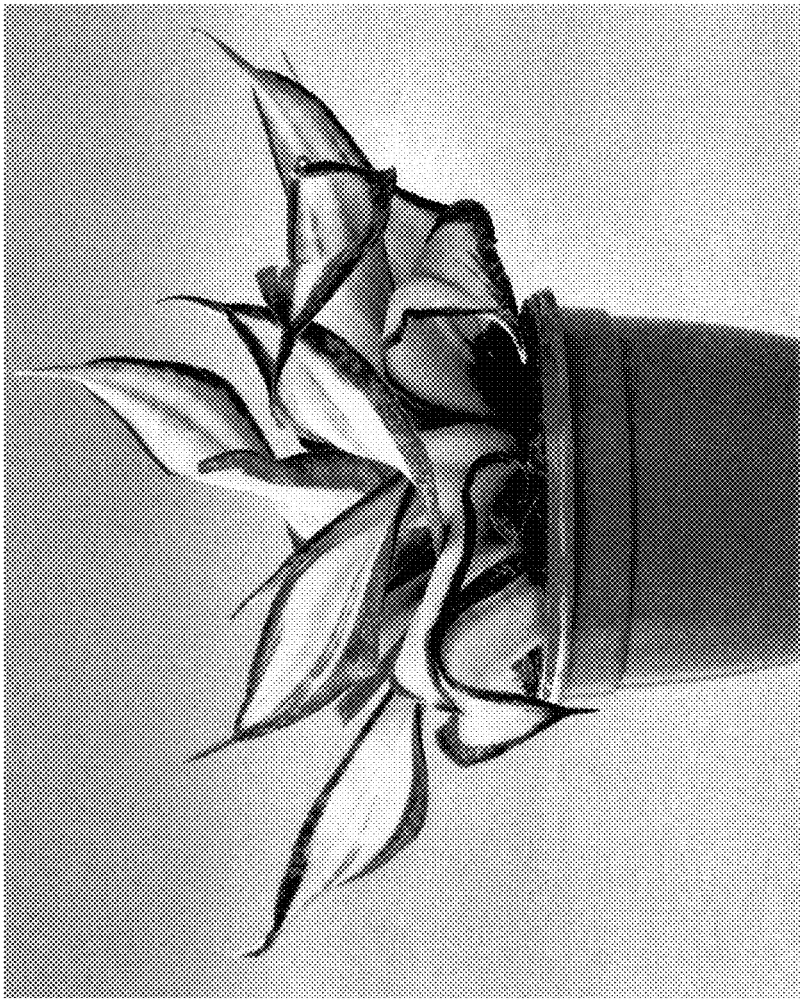
FIG. 2 is a side view of the plant in FIG. 1, showing the vertically compressed spiral rosette.
Figure 3:
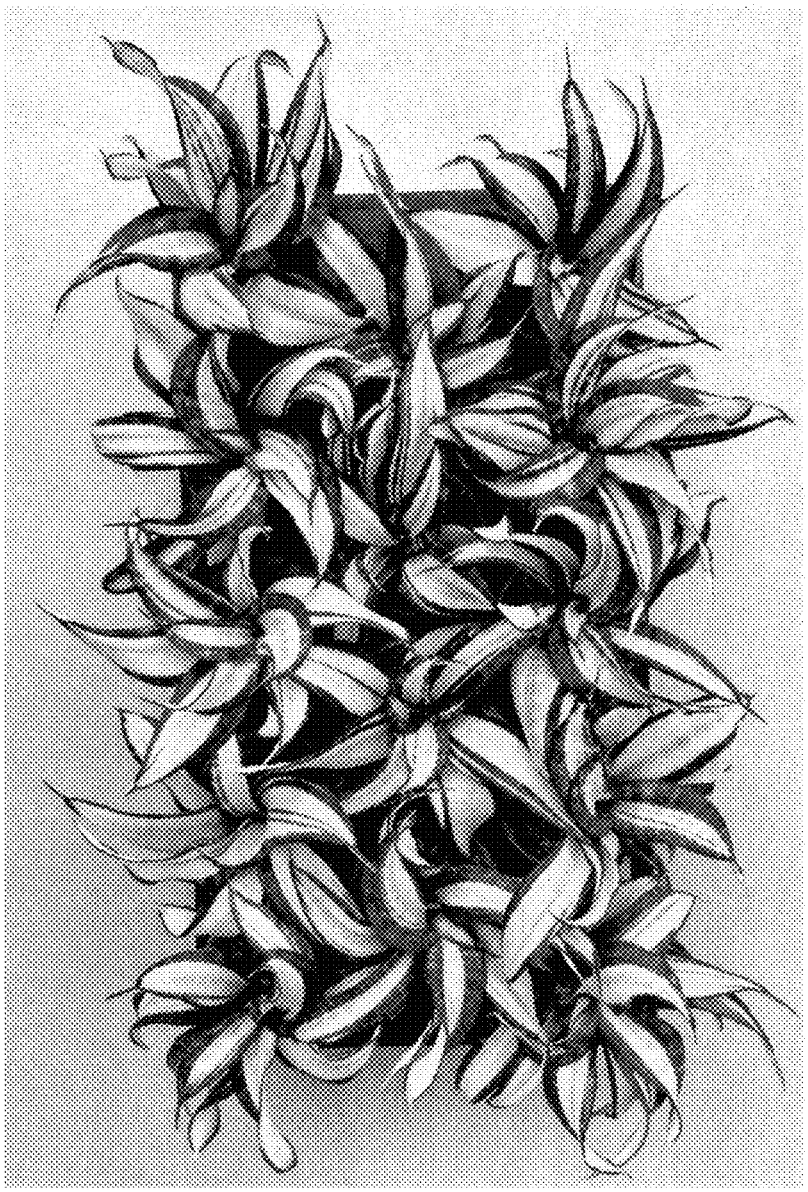
FIG. 3 Shows a group of 14 'HANSOTI44' plants in a tray, showing uniformity across multiple plants of this new cultivar.
Figure 4:
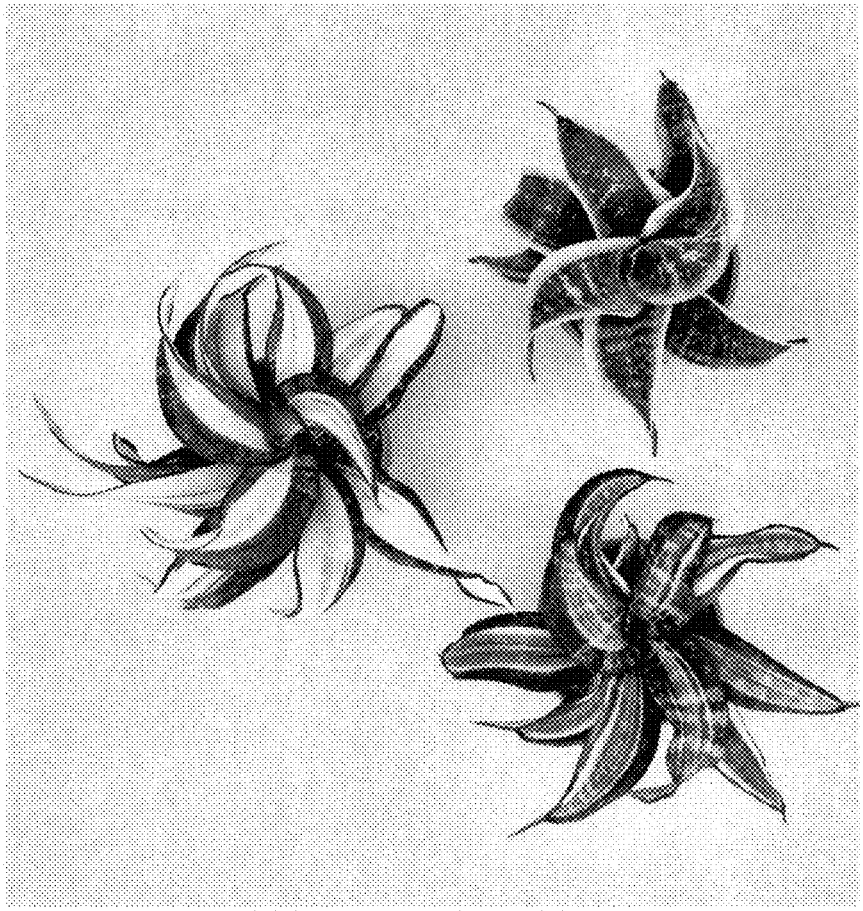

FIG. 4 'Hansoti44' (Top Center) with the parental cultivar 'Hansoti41' (Bottom Left) and the comparator cultivar 'Hansoti21' (Bottom Right).

Figure 5:
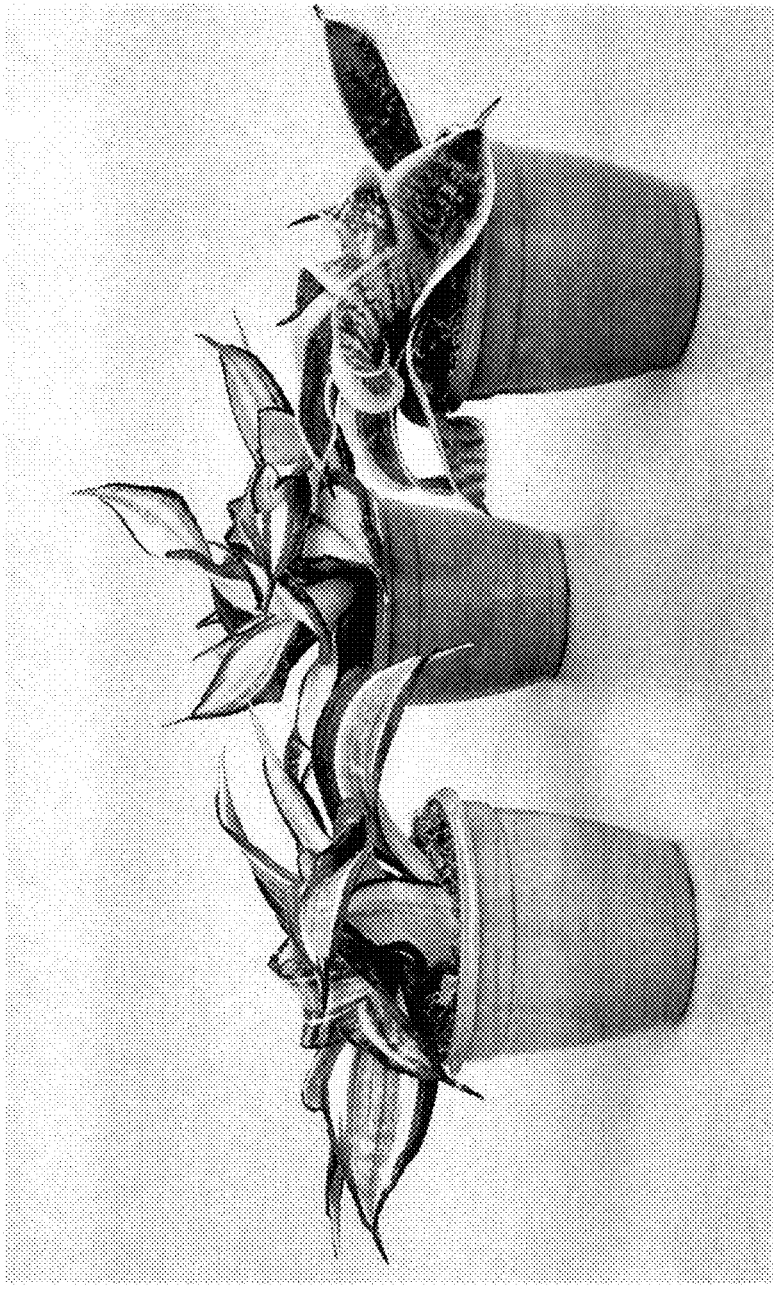

FIG. 5 shows the same three cultivars as in FIG. 4 but from the side to illustrate the spiral and vertically flattened spiral rosette of all three but with very different and unique variegation pattens and colours.

Figure 6:
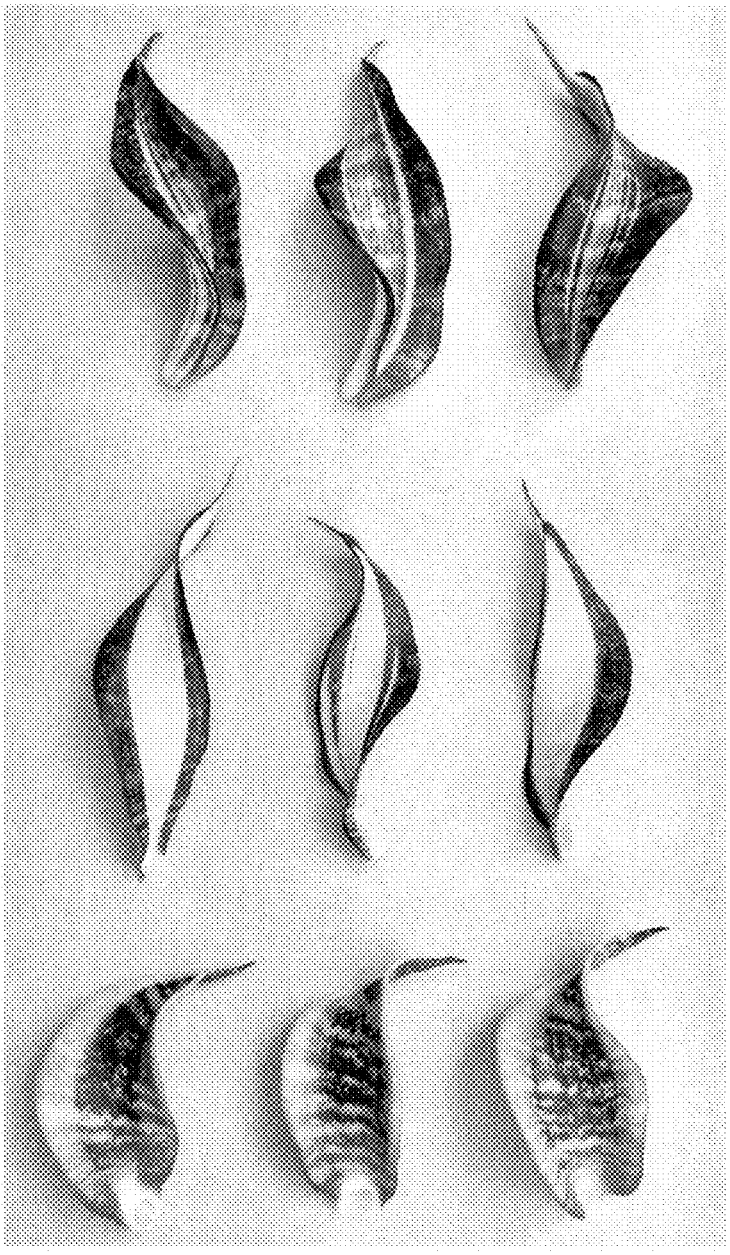

FIG. 6 shows a comparison of the upper surface of individual leaves of *Sansevieria trifasciata* 'Hansoti44' (Middle Row) with the Parental cultivar 'Hansoti41' on the top row and comparator cultivar 'Hansoti21' on the bottom row. Leaves of all three are twisted and curved but differ in variegation pattern & coloration.

DETAILED BOTANICAL DESCRIPTION

The new *Sansevieria* 'HANSOTI44' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI44' plants grown in an open poly house (high tunnel) at Village Asle, District Satara, Maharashtra State in Western India. Average temperature in Asle is 25° C., with summer highs of 39° C. and winter lows of 6° C. Plants grow under natural light conditions and between 30% to 75% shade levels depending on the season (higher shade in hot summer conditions).

This crop gets nearly constant fertilization to increase production. Controlled release fertilizer 13:11:11 Type 360-days release at 1 kilo/cubic meter of media, Constant Liquid Feed at approximately 100 ppm N, 20 ppm P and 100 ppm K, along with complete micronutrients. Production is closely related with proper and complete plant nutrition and an open soilless growing media based on coconut coir. The plants are grown in plastic pots on metal benching in spacing trays.

Color references are made to The Royal Horticultural Society Colour Chart (R.H.S.), (April 2009) except where general colors of ordinary significance are used.

The photographs and descriptions were taken during the monsoon season in Asle, District Satara, Maharashtra State, India when outdoor day temperature was 32° C. to 38° C., and nighttime temperatures of 25° C. to 28° C. The age of the plants described is 3-4 months.

Botanical classification: *Sansevieria trifasciata* 'HANSOTI44'.

General information:

*Parentage.*—*Sansevieria trifasciata* 'Hansoti41', unpatented.

*Optimal growth conditions.*—

*Light intensities.*—High adaptability to outdoor or indoor conditions.

*Temperature.*—Day: 25° C. to 35° C. Night: 15° C. to 25° C.

*Temperature tolerance.*—Tolerant to a low temperature of about 6° C. and a high temperature of 38° C. and above — very heat tolerant.

*Fertilization.*—Constant feed of 100 ppm N, 20 ppm P and 100 ppm K is used along with micronutrients with occasional leaching. Media incorporation of 13:11:11 Type 360 Days release at 1 kg/cubic meter of media.

*Growth regulators.*—Not necessary for growth, however rooting hormone aids in rapid and prolific rooting of offsets.

Propagation:

*Typical.*—Vegetative, by side suckers which come true to type. Does not come true from leaf cuttings.

*Rooting habit and description.*—Rhizomes are elongated, fleshy, giving rise to offsets (side shoots). Offsets root easily with fibrous adventitious roots from cut end. Rooting hormone helps in faster and more prolific rooting. Colored cream to brown, not accurately measured with R.H.S. chart.

*Time to initiate roots.*—15 to 20 days at 25° C. to 30° C.

*Time to produce a rooted liner.*—About 45 days at 25° C. to 30° C.

*Time to produce ready* 12 *cm potted plant from liner.*—About 3 months at 25° C. to 30° C.

Plant:

*General appearance and form.*—Monocot; leaf bases arranged in a rosette around growth point.

*Height.*—About 10 to 12 cm when grown in 12 cm pots.

*Spread.*—About 17 to 20 cm when grown when grown in a 12 cm size container.

*Growth rate and habit.*—Moderate growth rate, stays flat and compact.

*Shape.*—Rosette.

*Fragrance.*—None.

*Stem.*—Modified (rhizomes which are fleshy with erect foliage, branching and giving offsets so forming clumps in time).

*Rosette height.*—About 6 to 8 cm height from top of pot when grown in 12 cm size container.

*Rosette diameter.*—About 16 cm to 18 cm.

*Texture*.—Smooth, waxy.
*Colour*.—As described above.
*Strength*.—Strong and durable.
*Internode length*.—About 1 mm.

Foliage:

*Quantity*.—About 10 to 12 in ready to sell plant. Number slowly increases with age.
*Arrangement and attachment*.—Single, alternate; leaf bases arranged stiffly in a rosette around central growth point.
*Leaf length*.—About 11 to 13 cm, full-size leaf.
*Leaf width*.—About 5 to 8 cm, full-size leaf.
*Overall shape of leaf*.—Lanceolate.
*Apex shape*.—Acute, triangular and aristate, with soft tip.
*Base shape*.—Plane.
*Margin*.—Sharp, smooth.
*Texture*.—Upper Surface: Smooth and waxy texture.
*Texture*.—Under Surface: Smooth and waxy texture.
*Pubescence*.—None.
*Color of mature leaf*.—Upper Surface: Border band of dark green colour near RHS Green 136A with cream central area near Yellow 4B.
*Margins*.—Dark olive green near RHS Green 136A. Full details of leaf coloration is given above in the description of the invention.
*Venation*.—Pattern: Longitudinal/parallel leaf shape.
*Venation color*.—Indistinguishable from leaf blade.
*Leaf fragrance*.—None.

Other:

*Inflorescence description*.—Flowers not observed to date.
*Weather resistance*.—Moderately drought tolerant.
*Pest resistance*.—Reasonably resistant to pests, susceptible to root mealybugs (*Rhizoecus pritchardi*). Typical pests include *Pseudococcidae longispinus* and *Tetranychus urticae*.
*Disease resistance*.—Occasionally shows Anthracnose and leaf spots but largely disease-free from clean mother stock.
*Fruit/seed production*.—No fruits/seeds detected to date.

What is claimed is:

1. A new and distinct cultivar of *Sansevieria* plant named 'HANSOTI44' as herein illustrated and described.

* * * * *